United States Patent [19]
Spears

[11] Patent Number: 5,086,620
[45] Date of Patent: Feb. 11, 1992

[54] METHOD OF MICROENCAPSULATION OF HYPERBARIC GAS

[75] Inventor: James R. Spears, Bloomfield Hills, Mich.

[73] Assignee: Wayne State University, Detroit, Mich.

[21] Appl. No.: 655,078

[22] Filed: Feb. 14, 1991

[51] Int. Cl.[5] ............................................. F25B 19/00
[52] U.S. Cl. .......................................... 62/51.1; 62/78
[58] Field of Search ................................... 62/51.1, 78

[56] References Cited

U.S. PATENT DOCUMENTS

| | | |
|---|---|---|
| 3,963,503 | 6/1976 | Mackenzie . |
| 3,972,721 | 8/1976 | Hammel et al. . |
| 4,104,074 | 8/1978 | Rostoker . |
| 4,332,907 | 6/1982 | Vieli . |
| 4,332,908 | 6/1982 | Vieli . |
| 4,347,326 | 8/1982 | Iwami et al. . |
| 4,658,601 | 4/1987 | Burchell et al. ...................... 62/51.1 |

Primary Examiner—Ronald C. Capossela
Attorney, Agent, or Firm—Brooks & Kushman

[57] ABSTRACT

Method of encapsulating a hyperbaric gas for the treatment of diseases in humans with encapsulated gaseous precursors, such as microbubbles of oxygen. The method includes the step of immersing a receptacle containing an encapsulating material into a reaction vessel. An ultrasonic probe is then inserted into the reaction vessel. When the vessel is sealed, a source of hyperbaric gas is communicated therewith, and the vessel is then immersed within a cooling fluid so that the hyperbaric gas condenses. Thermal energy is then applied to the receptacle and ultrasound energy is delivered to the ultrasonic probe. When the probe vibrates, hyperbaric gas is distributed within the heated encapsulating material. After the cooling fluid chills the mixture of hyperbaric gas in the encapsulating material, the hyperbaric gas is entrapped therewithin. The encapsulated oxygen precursor can be used to treat atherosclerosis, infections and neoplasms, as well as to provide systemic oxygenation of tissues.

38 Claims, 2 Drawing Sheets

METHOD OF MICROENCAPSULATION OF HYPERBARIC GAS

BACKGROUND OF THE INVENTION

1. Field Of Invention

The present invention relates generally to a sonication method of encapsulating a hyperbaric gas for use in treating atherosclosis, infections and neoplasms, and for providing systemic oxygenation of tissues.

2. Related Art Statement

Most living organisms require oxygen to maintain homeostasis and viability. Tissues in man and other mammals are oxygenated by virtue of the dissolution and binding of oxygen in blood within capillaries of the lung after diffusion of oxygen across thin alveolar membranes of the lung. The quantity of oxygen bound to hemoglobin and, to a lesser extent, dissolved within serum is usually adequate to maintain an optimal level of oxygenation of all tissues by diffusion of oxygen from blood capillaries to tissue. Although the rate of diffusion of oxygen through soft tissues is actually quite slow, the intercapillary distance is usually small, so that only very short diffusional distances are required, For some tissues, however, the diffusional distances for oxygen are large, and local tissue hypoxia results. The lack of an optimal supply of oxygen interferes with local tissue homeostasis, and pathologic tissue growth is initiated and/or promoted.

Efforts have been made to improve blood oxygenation by inspiration of oxygen at higher than normal oxygen concentration in air. These efforts have not been satisfactory factory because: 1) prolonged inspiration of oxygen at a high partial pressure produces lung toxicity, and 2) blood is nearly saturated with oxygen during ordinary air breathing—accordingly, an increase in the inspired oxygen concentration above that in air does little to increase the content of oxygen within blood.

One approach to problems of improving blood oxygenation would be to encapsulate oxygen under pressure in a manner which allows parenteral injection of oxygen. Gas-containing capsules have been prepared from a variety of substances, including glass. Methods to make such glass particles are known. By way of example, one method is disclosed in U.S. Pat. No. 3,972,721 to Hammel et al, entitled "Thermally Stable and Crush Resistant Microporous Glass Catalyst Supports and Methods of Making", the relevant teachings of which are incorporated herein by reference. The technology presently exists for the manufacture of hollow glass microballoons as small as two microns. For example, FTF-15 glass microballoons can be purchased from Emerson and Cumming of W.R. Grace, Inc. Thus, it is feasible to make hyperbaric gas-filled glass microballoons sufficiently small to pass through all capillaries of the body (approximately 5 microns in diameter) without entrapment following intravenous injection of a suspension of the glass shells. However, only low molecular weight gases such as helium can permeate the glass shells during heating of the latter under hyperbaric gas conditions, so that the gas will be trapped within the microballoons upon subsequent cooling of the glass. Since the permeability of higher molecular weight gases through glass even at elevated temperatures is quite low, a sufficient quantity of oxygen cannot be entrapped.

One method for forming fine glass foam is disclosed in U.S. Pat. No. 4,332,907 to Vieli entitled "Granulated Foamed Glass and Process for the Production Thereof", filed Oct. 4, 1979, the relevant teachings of which are incorporated herein by reference. Another method is disclosed in U.S. Pat. No. 3,963,503, entitled "Method of Making Glass Products, Novel Glass Mix and Novel Glass Product", the relevant teachings of which are also incorporated herein by reference. U.S. Pat. No. 4,347,326 to Iwami et al entitled "Foamable Glass Composition and Glass Foam", filed Aug. 31, 1982, the relevant disclosure of which is also incorporated herein by reference, also teaches a method for making a glass foam. See also, U.S. Pat. No. 4,332,908 to Vieli filed Nov. 27, 1979 entitled "Foamed Granular Glass", and U.S. Pat. No. 4,104,074 entitled "Pulverulent Borosilicate Composition and a Method of Making a Cellular Borosilicate Body Therefrom", the relevant teachings of which patents are also incorporated herein by reference.

However, none of those methods are capable of viably producing sufficiently small microbubbles to permit injection, containing gases at sufficiently high pressures which are critical to the process disclosed below.

Accordingly, it is an object of the present invention to provide a method for encapsulating hyperbaric oxygen in order to treat diseases associated with hypoxia of tissues.

It is also an object of the present invention to provide products made by the disclosed process.

SUMMARY OF THE INVENTION

The present invention relates to a novel method for encapsulating a hyperbaric gas, such as oxygen in a form capable of being delivered to biological tissues. The method includes the step of immersing a receptacle containing an encapsulating material into a reaction vessel. An ultrasonic probe is then inserted into the reaction vessel. When the vessel is sealed, a source of hyperbaric gas is communicated therewith, and the vessel is then immersed within a cooling fluid so that the hyperbaric gas condenses. Thermal energy is then applied to the receptacle and ultrasound energy is delivered to the ultrasonic probe. When the probe vibrates, hyperbaric gas is distributed within the heated encapsulating material. After the cooling fluid chills the mixture of hyperbaric gas in the encapsulating material, the hyperbaric gas is entrapped therewithin.

In the preferred embodiment, hyperbaric oxygen or an alternative oxygen precursor is encapsulated in a particle size sufficiently small to permit intravascular injection without entrapment within tissue capillaries. Examples of an alternate oxygen precursor include sodium superoxide, potassium superoxide, and hydrogen peroxide. After delivery and dissolution, the particles liberate oxygen into specific tissue sites. The preferred encapsulating media include ice, clathrate hydrates, non-hydrate clathrates, and or water-soluble glasses. The controlled release of oxygen facilitates the diagnosis and treatment of many diseases. Examples of such application include treatment of atherosclerosis, the treatment of infections, the treatment of neoplasms, systemic oxygenation of tissues, and employment as an echogenic contrast agent.

BEST MODES FOR CARRYING OUT THE INVENTION

Figure 1:
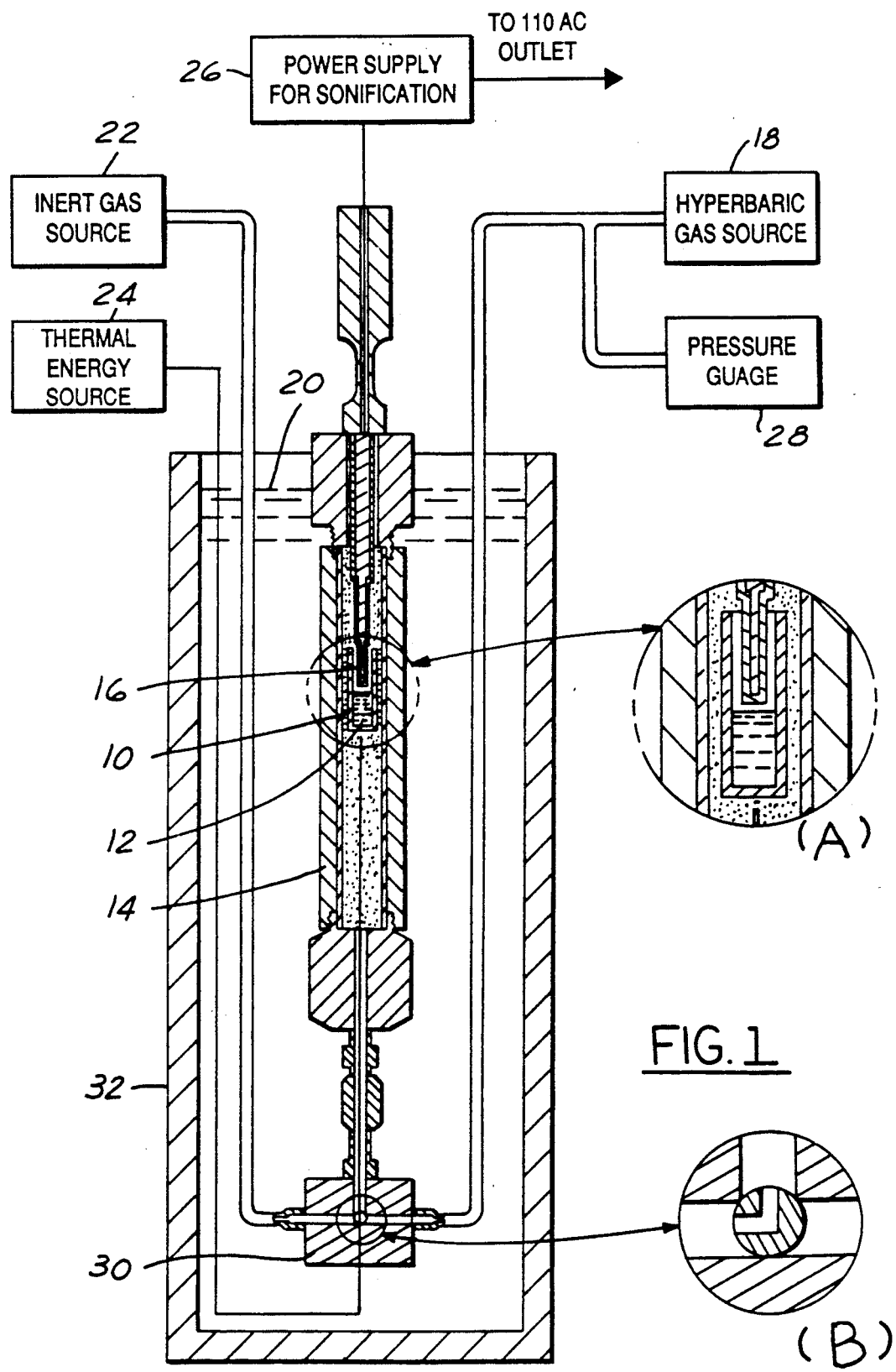
FIG. 1 is a sectioned view of an apparatus used to encapsulate a hyperbaric gas according to the teachings of the present invention.

Turning first to FIG. 1, there is depicted in schematic form an apparatus used for practicing the present invention.

Shown in FIG. 1 is a receptacle 10 of encapsulating material 12, the receptacle 10 being supported within a hollow reaction vessel 14. An ultrasonic probe 16 is disposed so that its tip is located in juxtaposition with the encapsulating material 12. Energy is supplied to the ultrasonic probe 16 from a power supply 26.

Located in communication with the reaction vessel 14 is an adapter 30 through which a conduit is provided to a source of hyperbaric gas 18. To monitor the pressure of such gas, a pressure gauge 28 is provided.

Also in communication with the reaction vessel 14 is a source of thermal energy 24 which may be used selectively to heat the reaction vessel 14 and its contents.

A container 32 provides a reservoir of cooling fluid 20 within which the adapter 30, the reaction vessel, and its contents are immersed.

Figure 2:
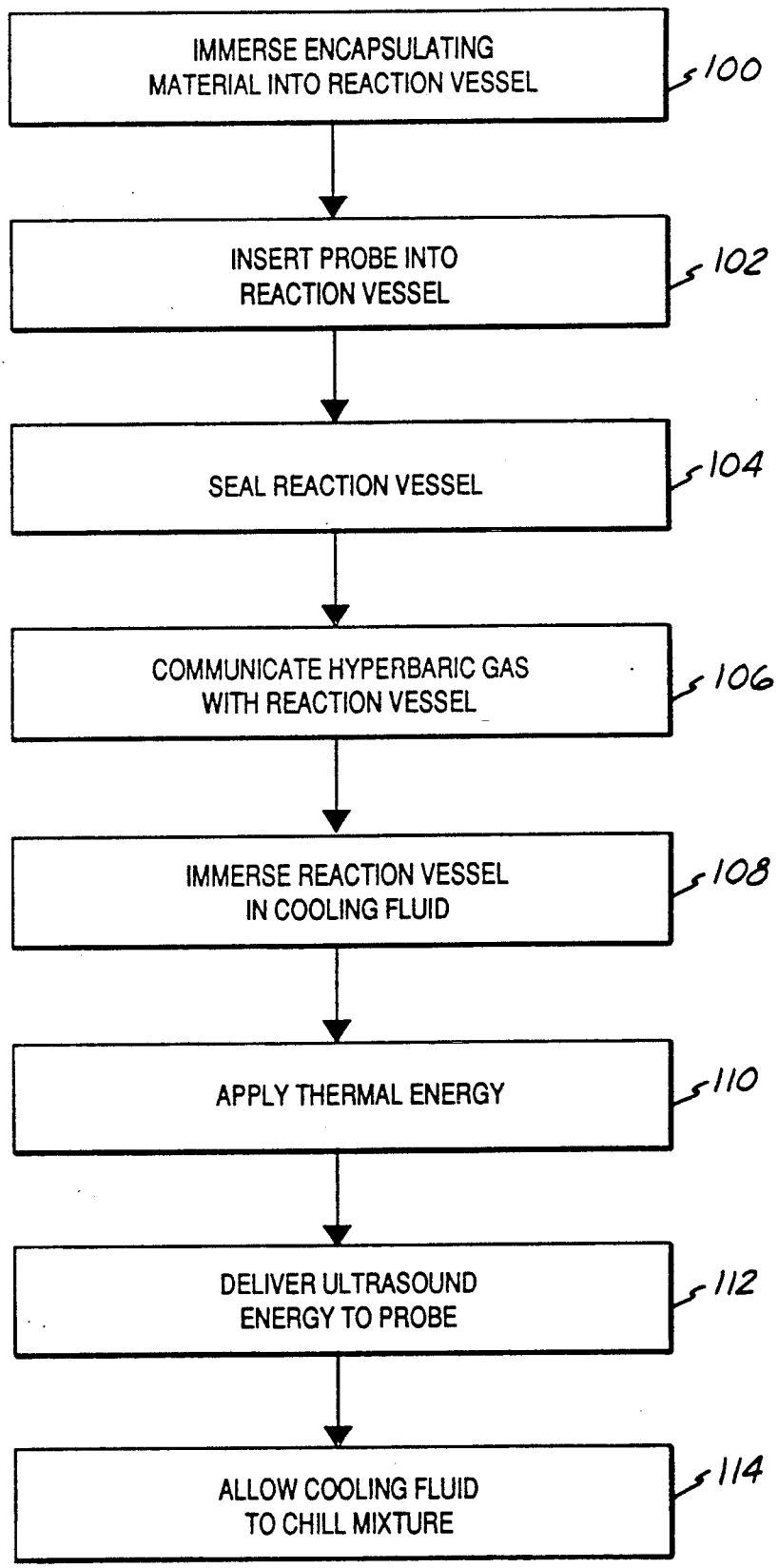
FIG. 2 is a flow chart indicating method steps involved in practicing the present invention.

Turning now to FIGS. 1 and 2 taken together, it can be seen that there is disclosed a method of encapsulating a hyperbaric gas. The encapsulating material 12 is added to the receptacle 10, which is supported within the reaction vessel 14. The ultrasonic probe 16 is then inserted into the reaction vessel 14 so that a portion of the ultrasonic probe 16 is juxtaposed to the encapsulating material 12. After insertion of the ultrasonic probe 16 into the reaction vessel, the reaction vessel 14 is sealed, so that the receptacle 10 and the ultrasonic probe 16 are entrapped therewithin. The source of hyperbaric gas 18 is then communicated through the adapter 30 into the reaction vessel 14 so that a space between the encapsulating material 12 and the ultrasonic probe 16 is permeated thereby.

The reaction vessel 14 is immersed at least partially within the reservoir of cooling fluid 20 within the container 32 so that the hyperbaric gas condenses within the reaction vessel 14 upon exposure to a cold environment created by the cooling fluid. For encapsulating media having melting points greater than about 25° C., chilling the reaction vessel is unnecessary when oxygen pressures less than about 3,000 psi are used. Thermal energy is then applied to the receptacle 10 from the thermal energy source 24 so that the encapsulating material 12 is heated thereby.

To distribute the hyperbaric gas within the heated encapsulating material 12, ultrasound energy is delivered from the power supply 26 through the ultrasonic probe 16 so that the probe is vibrated thereby.

After allowing the cooling fluid 20 to chill the mixture of hyperbaric gas and the encapsulating material 12, the hyperbaric gas is entrapped therewithin, thereby forming a hyperbaric gas-enriched encapsulating material.

The process disclosed above can also be supplemented by the step of communicating the source of inert gas 22 under a higher pressure with the reaction vessel 14 so that a super high pressure environment surrounds the ultrasonic probe 16, the encapsulating material 12, and the hyperbaric gas.

Having disclosed the broad method steps, additional detail of the various steps will now be provided.

While various encapsulating materials 12 have been considered, good results have been found when the encapsulating material 12 is selected from a group consisting of water, ice, an inorganic salt, a carbohydrate, a phosphate glass, urea, hydroquinone, and mixtures thereof. Where the encapsulating material 12 is ice, similar results have been obtained when the ice is enriched with deuterium oxide. Alternatively, the encapsulating material 12 may be water, enriched by deuterium oxide. More specifically, the encapsulating material 12 may be an ice selected from a group consisting of cubic Type I ice, hexagonal Type I ice, Type II ice, Type V ice, Type VI ice, Type IX ice, vitreous ice, and mixtures thereof.

Preferably, the hyperbaric gas is oxygen, although the method of the present invention can be practiced with other gaseous forms, such as hydrogen peroxide ($H_2O_2$). Alternatively, the hyperbaric gas is selected from a group consisting of oxygen, oxygen radicals, singlet oxygen, or any combination of oxygen moieties.

The step of applying thermal energy can be achieved by providing a source of laser energy, or by an electrical heating source.

While good results have been obtained when the receptacle 10 is formed from platinum, it will be appreciated that other Group VII metals, silica-based glasses, and other inert materials are suitable for this purpose.

Preferably, the ultrasonic probe 16 is formed from titanium for sonication. To enhance its performance when used at elevated temperatures, a gold coating may be applied to the titanium probe. However, the ultrasonic probe 16 may also be formed from suitable equivalents, such as those found in other Group IV metals.

In the preferred embodiment of the apparatus used to practice the present invention, cooling fluid 20 comprises liquid nitrogen.

The hyperbaric gas source 18 is capable of delivering oxygen, for example, at pressures between about 2,000-100,000 psi, as registered on the pressure gauge 28. Isolation of the reaction vessel from the source of gas and subsequent application of thermal energy to chilled reaction vessel component(s) in contact with chilled gas results in a further pressure rise when the gas warms. At elevated pressures, some portion of the hyperbaric gas is dissolved within the encapsulating material 12 before sonication. After sonication and cooling the encapsulating material, the hyperbaric gas becomes entrapped within the encapsulating material. Examination has shown that hyperbaric gas exists in the form of bubbles with a mean diameter of less than about 100 microns, and additional gas is further dissolved in the encapsulating material.

The hyperbaric gas, which is preferably oxygen, may also be entrapped within the encapsulating material 12 as a clathrate, wherein individual gas molecules are entrapped within molecular cages of the encapsulating material. In an alternative mode of practicing the present invention, the clathrate may be a hydrate.

The product formed from the disclosed process takes the form of hyperbaric gas-enriched encapsulating material, which is removed from the reaction vessel 14 after sonication and is pulverized into a powder having granules of a mean diameter less than about 100 microns.

An alternative step in practicing the present invention involves the provision of an immiscible liquid provided within the receptacle 10. Following this approach, the step of delivering ultrasound energy comprises sonicating in juxtaposition with the immiscible liquid, thereby producing a suspension of granules of the encapsulating material 12 within the immiscible liquid upon cooling. In use, the immiscible liquid is subsequently removed from the granules of hyperbaric gas-enriched encapsulating material, thereby producing a free-flowing powder.

If an immiscible liquid is not used, a solvent may be provided to produce small granules of the gas-enriched encapsulating material by exposing the gas-enriched encapsulating material partially to the solvent. In use, the solvent may be removed from the hyperbaric gas-enriched encapsulating material to produce a free-flowing powder thereof. In use, the small granules including hyperbaric gas-enriched encapsulating material are injected intravenously in vivo, thereby promoting contact with body tissues and a release of oxygen. While alternative forms of encapsulating material have been disclosed earlier, it should be appreciated that alternative encapsulating materials 12 may be used. For example, the encapsulating material 12 may be water in the form of water of hydration within a non-aqueous compound, or water which includes approximately 5g % dextrose dissolved therein. The non-aqueous compound may be selected from a group consisting of an inorganic salt, a carbohydrate, a protein, a phosphate glass, and mixtures thereof. When the gas is entrapped in the form of a clathrate, examples of encapsulating materials include ice, urea, and hydroquinone.

Where the encapsulating material 12 is ice, the disclosed method may be supplemented by the step of providing an aqueous carrier at about 0° C. to about 37° C. to facilitate transport of powdered ice. Alternatively, injection of the powdered ice may be facilitated by fluid transport with a non-aqueous fluid, such as ethanol, propylene glycol, glycerol, and supercritical carbon dioxide. Where the encapsulating material 12 is powdered ice, the ice melts upon contact with blood, thereby releasing microbubbles of oxygen which rapidly disappear as a result of the of affinity of oxygen for hemoglobin and dissolution in plasma.

Results have shown that the hyperbaric gas-enriched encapsulating material may include microbubbles having an average size of between about 0.01 and about 3.00 microns in diameter. To further provide a controlled, slow-release mixture of hyperbaric gas, it is possible to coat the particles of gas-enriched encapsulating material with another material having a slower rate of dissolution.

In the preferred embodiment of the process disclosed, the inert gas comprises a mixture selected from the group consisting of argon, helium, and mixtures thereof.

Where ice is the encapsulating material, the process steps contemplated by the present invention may include the use of polymorph(s) having a melting point higher than 0° C. Where this is the case, injection of such ice into the bloodstream tends to delay the liberation of hyperbaric gas therefrom.

Earlier, it was noted that thermal energy is delivered to the receptacle 10 on the thermal energy source 24. In one embodiment, a fiber optic formed from Group VIII metal is employed to deliver such thermal energy to the encapsulating material 12.

In practice, the step of delivering ultrasonic energy comprises the step of delivering such energy in a frequency within a 20 hertz to 200 kilohertz range.

As a result of the process disclosed, the product prepared therefrom comprises a hyperbaric gas captured within an encapsulating material which yields greater than about 20cc's of gas per gram of encapsulating material and liberated therefrom under atmospheric pressure.

Thus, in order to be used in hypoxic tissue to treat disease or diagnose disease, the oxygen precursor has been encapsulated to avoid the problems of the prior art. As is now apparent, encapsulation in the present invention refers to any process which physically or chemically binds or traps the oxygen precursor in a manner which allows release of the oxygen precursor from the encapsulating material at a predetermined rate after administration of the capsules into mammalian tissue. In the primary embodiment of the present invention, either hyperbaric oxygen or hydrogen peroxide is micro- or nano-encapsulated in order to achieve a slow release of this drug into biological tissues.

Having above indicated a preferred embodiment of the present invention, it will occur to those skilled in the art that modifications and alternatives can be practiced within the spirit of the invention. It is accordingly intended to define the scope of the invention only as indicated in the following claims.

What is claimed is:

1. A method of encapsulating a hyperbaric gas, comprising the steps of:
   supporting within a reaction vessel a receptacle containing an encapsulating material;
   inserting an ultrasonic probe into the reaction vessel so that a portion of the ultrasonic probe is juxtaposed to the encapsulating material;
   sealing the reaction vessel so that the receptacle and the ultrasonic probe are entrapped therewithin;
   communicating a source of the hyperbaric gas with the reaction vessel so that a space between the encapsulating material and the ultrasonic probe is permeated thereby;
   immersing the reaction vessel at least partially within a cooling fluid so that the hyperbaric gas condenses within the reaction vessel upon exposure to a cold environment created by the cooling fluid;
   applying thermal energy to the receptacle so that the encapsulating material is heated thereby;
   delivering ultrasound energy to the ultrasonic probe so that the probe is vibrated, thereby distributing hyperbaric gas within the heated encapsulating material; and
   allowing the cooling fluid to chill the mixture of hyperbaric gas and the encapsulating material so that the hyperbaric gas is entrapped within the encapsulating material, thereby forming a hyperbaric gas-enriched encapsulating material.

2. The method of claim 1, further including the step of communicating a source of inert gas under a high pressure with the reaction vessel so that a super high pressure environment surrounds the ultrasonic probe, the encapsulating material, and the hyperbaric gas.

3. The method of claim 2, wherein the inert gas comprises a gas selected from the group consisting of argon, helium, and mixtures thereof.

4. The method of claim 1, wherein the encapsulating material is selected from a group consisting of water, ice, an inorganic salt, a carbohydrate, a phosphate glass, urea, hydroquinone, and mixtures thereof.

5. The method of claim 1, wherein the encapsulating material is ice which is enriched with deuterium oxide.

6. The method of claim 1, wherein the encapsulating material is an ice selected from a group consisting of cubic Type I ice, hexagonal Type I ice, Type II ice, Type V ice, Type VI ice, Type IX ice, vitreous ice, and mixtures thereof.

7. The method of claim 1, wherein the hyperbaric gas is oxygen.

8. The method of claim 1, wherein the step of applying thermal energy is provided by an electrical heating source.

9. The method of claim 1, wherein the step of applying thermal energy is provided by a source of laser energy.

10. The method of claim 1, wherein the step of applying thermal energy is provided by electrical energy.

11. The method of claim 1, wherein the receptacle comprises a Group VII metal.

12. The method of claim 1, wherein the ultrasonic probe comprises a Group IV metal.

13. The method of claim 1, wherein the cooling fluid comprises liquid nitrogen.

14. The method of claim 1, wherein the hyperbaric gas is dissolved within the encapsulating material.

15. The method of claim 1, wherein the hyperbaric gas entrapped within the encapsulating material exists about 100 microns.

16. The method of claim 1, wherein the hyperbaric gas is entrapped within the encapsulating material as a clathrate.

17. The method of claim 16, wherein the clathrate is a hydrate.

18. The method of claim 1, wherein the hyperbaric gas-enriched encapsulating material is removed from the reaction vessel and pulverized into a powder having granules with a mean diameter of less than about 100 microns.

19. The method of claim 1, wherein the step of delivering ultrasound energy comprises sonicating in juxtaposition with an immiscible liquid, thereby producing a suspension of granules of the encapsulating material within the immiscible liquid upon cooling.

20. The method of claim 19, wherein the immiscible liquid is subsequently removed from the granules of hyperbaric gas-enriched encapsulating material, thereby producing a free-flowing powder.

21. The method of claim 1, further comprising the step of providing a solvent, within which partial dissolution of the gas-enriched encapsulating material is arrested to produce small granules of the gas-enriched encapsulating material.

22. The method of claim 21, wherein the solvent is removed to produce a free-flowing powder of the hyperbaric gas-enriched encapsulating material.

23. The method of claim 1, further including the step of injecting hyperbaric gas-enriched encapsulating material intravenously in vivo, thereby promoting contact with body tissues and a release of oxygen.

24. The method of claim 1, wherein the encapsulating material is water enriched by deuterium oxide.

25. The method of claim 1, wherein the encapsulating material is water in the form of water of hydration within a non-aqueous compound.

26. The method of claim 25, wherein the non aqueous compound is selected from a group consisting of an inorganic salt, a carbohydrate, a protein, a phosphate glass, urea, hydroquinone, and mixtures thereof.

27. The method of claim 1, wherein the encapsulating material is water which includes approximately 5g % dextrose dissolved in the water.

28. The method of claim 1, wherein the encapsulating material is ice and includes the step of providing an aqueous carrier at about 0° C. to about 37° C. to facilitate transport of powdered ice.

29. The method of claim 1, wherein the encapsulating material is powdered ice which melts upon contact with blood, thereby releasing micro bubbles of oxygen which rapidly disappear as a result of the affinity of oxygen for hemoglobin and dissolution in plasma.

30. The method of claim 29, wherein injection of the powdered ice is facilitated by fluid transport with supercritical carbon dioxide.

31. The product of claim 1, wherein the hyperbaric gas-enriched encapsulating material includes micro bubbles having an average size of between about 0.01 microns and about 3.00 microns in diameter.

32. The product of claim 1, wherein particles of the hyperbaric gas-enriched encapsulating material are coated with a material having a slower rate of dissolution upon contact with water than that of the encapsulating material, thereby producing a controlled, slower-release preparation of hyperbaric gas.

33. A product prepared according to the method of claim 1, wherein the hyperbaric gas captured within the encapsulating material yields greater than about 20 cc's of gas per gram of encapsulating material when liberated therefrom under atmospheric pressure.

34. A method of encapsulating hyperbaric gas comprising the steps of:
   connecting a fiber optic to a receptacle formed of a Group VIII metal for delivery of thermal energy thereto;
   adding an encapsulating material to the receptacle;
   communicating a source of thermal energy to the fiber optic;
   placing the receptacle at least partially within a reaction vessel so that the receptacle and the encapsulating material are supported therewithin;
   inserting an ultrasonic probe so that the ultrasonic probe terminates in juxtaposition with the encapsulating material;
   securing the reaction vessel so that the probe, the receptacle, and the fiber optic are sealingly engaged therewithin;
   immersing the reaction vessel in a cooling fluid;
   introducing a gas into the reaction vessel so that the density of the gas increases upon exposure to a cold environment generated by the cooling fluid;
   activating the source of thermal energy in order to deliver such energy through the fiber optic to the encapsulating material;
   delivering ultrasonic energy to the ultrasonic probe, thereby promoting a rapid distribution of hyperbaric oxygen throughout the encapsulating material during sonication; and
   discontinuing the supply of thermal and ultrasonic energy and allowing the hyperbaric gas-enriched encapsulating material to cool, thereby entrapping the hyperbaric gas within the encapsulating material.

35. The method of claim 34, further comprising the step of communicating an inert gas into the reaction vessel so that the pressure therein rises to about 50,000 psi.

36. The method of claim 34, wherein the step of delivering ultrasonic energy comprises the step of delivering such energy at a frequency within a 20 hertz to 200 kilohertz range.

37. The method of claim 34, wherein the hyperbaric gas is selected from a group consisting of oxygen, oxygen radicals, singlet oxygen, or any combination of oxygen moieties.

38. The method of claim 34, further comprising the step of at least partially dissolving the hyperbaric gas-enriched encapsulating material in a solvent so that granules containing micro bubbles are produced; and arresting the dissolution step when granules of an appropriate size are reached.

* * * * *

UNITED STATES PATENT AND TRADEMARK OFFICE
CERTIFICATE OF CORRECTION

PATENT NO. : 5,086,620
DATED : February 11, 1992
INVENTOR(S) : James R. Spears

It is certified that error appears in the above-indentified patent and that said Letters Patent is hereby corrected as shown below:

Column 1, line 1, after the title, insert the paragraph

--This invention was made with Government support, under Contract No. HL33252 awarded by the National Institutes of Health. The Government has certain rights in the invention.--

Signed and Sealed this

Fifth Day of October, 1993

Attest:

BRUCE LEHMAN

*Attesting Officer*　　　*Commissioner of Patents and Trademarks*